United States Patent
Tsurumune

(10) Patent No.: US 9,019,598 B2
(45) Date of Patent: Apr. 28, 2015

(54) LIGHT STIMULUS APPARATUS AND OBSERVING APPARATUS WITH LIGHT CONTROLLING UNIT

(75) Inventor: Atsushi Tsurumune, Odawara (JP)

(73) Assignee: Nikon Corporation, Tokyo (JP)

( * ) Notice: Subject to any disclaimer, the term of this patent is extended or adjusted under 35 U.S.C. 154(b) by 265 days.

(21) Appl. No.: 13/569,770

(22) Filed: Aug. 8, 2012

(65) Prior Publication Data

US 2012/0300295 A1 Nov. 29, 2012

Related U.S. Application Data

(60) Division of application No. 12/588,541, filed on Oct. 19, 2009, now Pat. No. 8,264,769, which is a continuation of application No. PCT/JP2008/001830, filed on Jul. 9, 2008.

(30) Foreign Application Priority Data

Jul. 17, 2007 (JP) ................................ 2007-185584
Jun. 23, 2008 (JP) ................................ 2008-162836

(51) Int. Cl.
*G02B 21/06* (2006.01)
*G02B 21/00* (2006.01)
*G01N 21/64* (2006.01)
*G02B 21/36* (2006.01)

(52) U.S. Cl.
CPC ........ *G02B 21/0032* (2013.01); *G01N 21/6456* (2013.01); *G02B 21/367* (2013.01)

(58) Field of Classification Search
None
See application file for complete search history.

(56) References Cited

U.S. PATENT DOCUMENTS

| | | | |
|---|---|---|---|
| 5,479,252 A * | 12/1995 | Worster et al. | ............. 356/237.5 |
| 6,282,019 B1 | 8/2001 | Kapitza | |
| 6,396,941 B1 | 5/2002 | Bacus et al. | |
| 6,958,858 B2 | 10/2005 | Engelhardt et al. | |
| 7,035,004 B2 | 4/2006 | Weiss | |

(Continued)

FOREIGN PATENT DOCUMENTS

EP    1 793 257 A1    6/2007
JP    A-2004-524532    8/2004

(Continued)

OTHER PUBLICATIONS

Feb. 9, 2010 International Preliminary Report on Patentability issued in corresponding International Application No. PCT/JP2008/001830 (with translation).

(Continued)

*Primary Examiner* — Arnel C Lavarias
(74) *Attorney, Agent, or Firm* — Oliff PLC

(57) ABSTRACT

A proposition is to reduce a waiting time during a light stimulus observation. In order to achieve the proposition, a light stimulus apparatus is characterized in that it includes a light path controlling unit that controls an irradiating position of light for stimulus on a specimen, and a controlling unit that generates a selected position signal of a selected position and an executive instruction signal for irradiation of the light for stimulus onto the specimen in conjunction with a confirm operation regarding the selected position performed by a pointing device on an image of the specimen displayed on a displaying unit, controls the light path controlling unit based on the selected position signal, and controls a light source which emits the light for stimulus based on the executive instruction signal.

6 Claims, 5 Drawing Sheets

(56) References Cited

U.S. PATENT DOCUMENTS

| | | |
|---|---|---|
| 7,227,112 B2 | 6/2007 | Storz |
| 7,486,886 B2 | 2/2009 | Endo et al. |
| 2004/0234451 A1 | 11/2004 | Tovar et al. |
| 2007/0120069 A1 | 5/2007 | Takamizawa |

FOREIGN PATENT DOCUMENTS

| | | |
|---|---|---|
| JP | A-2005-308985 | 11/2005 |
| JP | A-2005-337730 | 12/2005 |
| JP | A-2006-106346 | 4/2006 |
| JP | A-2007-93988 | 4/2007 |
| JP | A-2007-148223 | 6/2007 |

OTHER PUBLICATIONS

Japanese Office Action dated Jan. 31, 2012 for Japanese Application No. 2009-523532 (with translation).

Apr. 5, 2012 Extended European Search Report issued in European Application No. 08790182.3-2217.

* cited by examiner

LIGHT STIMULUS APPARATUS AND OBSERVING APPARATUS WITH LIGHT CONTROLLING UNIT

CROSS-REFERENCE TO RELATED APPLICATIONS

This application is a Divisional of application Ser. No. 12/588,541, filed Oct. 19, 2009, which is a Continuation of International Application PCT/JP2008/001830, filed Jul. 9, 2008, designating the U.S., and claims the benefit of priority from Japanese Patent Application No. 2007-185584 and No. 2008-162836, each filed on Jul. 17, 2007 and Jun. 23, 2008, the entire contents of which are incorporated herein by reference.

BACKGROUND

1. Field

The present application relates to an observing apparatus such as a confocal laser scanning microscope and a light stimulus apparatus applied to the observing apparatus.

2. Description of the Related Art

Patent Document 1: Japanese Unexamined Patent Application Publication No. 2007-93988 discloses a laser scanning microscope provided with an optical system for imaging and an optical system for light stimulus. The laser scanning microscope displays an image of a sample, allows a user to designate an area (which has a certain size) to which a light stimulus is to be applied on the image, and then starts to apply the light stimulus.

However, during a period of time from when the area is designated to when the application of light stimulus can be actually started, a circuit of the microscope has to calculate a drive waveform of a scanner based on coordinates of the area and to write the drive waveform into a memory for scanner. Accordingly, a waiting time for a user occurs.

Particularly, when the user repeatedly applies the light stimulus again and again while changing the areas, or when the designation of the areas and cancellation thereof are repeatedly conducted until the application of light stimulus is started, the waiting time frequently occurs.

Accordingly, the present application has a proposition to provide a light stimulus apparatus and an observing apparatus capable of reducing a waiting time during a light stimulus observation.

SUMMARY

A light stimulus apparatus of the present embodiment is characterized in that it includes a light path controlling unit that controls an irradiating position of light for stimulus on a specimen, and a controlling unit that generates a selected position signal of a selected position and an executive instruction signal for irradiation of the light for stimulus onto the specimen in conjunction with a confirm operation regarding the selected position performed by a pointing device on an image of the specimen displayed on a displaying unit, controls the light path controlling unit based on the selected position signal, and controls a light source which emits the light for stimulus based on the executive instruction signal.

Further, it is characterized in that the confirm operation regarding the selected position is a clicking operation of the pointing device.

Further, it is characterized in that the controlling unit sets an emitting pattern of the light emitted from the light source as a pattern previously designated by a user.

A light stimulus apparatus of the present embodiment is characterized in that it includes a light path controlling unit that controls an irradiating position of light for stimulus on a specimen, and a controlling unit that generates a selected position signal in conjunction with a position pointed by a pointing device on an image of the specimen displayed on a displaying unit, and controls the light path controlling unit in conjunction with the selected position signal.

Further, it is characterized in that the controlling unit makes the light emit in accordance with a clicking operation of the pointing device.

Further, it is characterized in that the controlling unit continues an operation of the controlling in conjunction with the selected position signal also during a non-emitting time of the light.

Further, it is characterized in that the controlling unit sets an emitting pattern of the light as a pattern previously designated by a user.

Further, it is characterized in that the emitting pattern is arbitrarily selected from a wavelength, an intensity, an irradiating time, an irradiating interval, a number of repeat, and a shape of the light for stimulus.

Further, it is characterized in that the controlling unit matches an emitting pattern of the light with a pattern of the clicking operation.

Further, an observing apparatus of the present embodiment is characterized in that it includes an optical imaging apparatus that obtains an image of the specimen, and the light stimulus apparatus according to any one of the aspects of the present embodiments that irradiates the light for stimulus onto the specimen.

Note that the imaging apparatus may be a scanning imaging apparatus provided with a light path controlling unit for imaging, and in such a case, it is preferable that the light path controlling unit of the light stimulus apparatus can be operated independently from the light path controlling unit for imaging.

According to the present application, a light stimulus apparatus and an observing apparatus capable of reducing a waiting time during a light stimulus observation are realized.

DETAILED DESCRIPTION OF THE EMBODIMENTS

[First Embodiment]

Hereinafter, a first embodiment will be explained. The present embodiment is an embodiment of a confocal fluorescence laser scanning microscope system.

Figure 1:
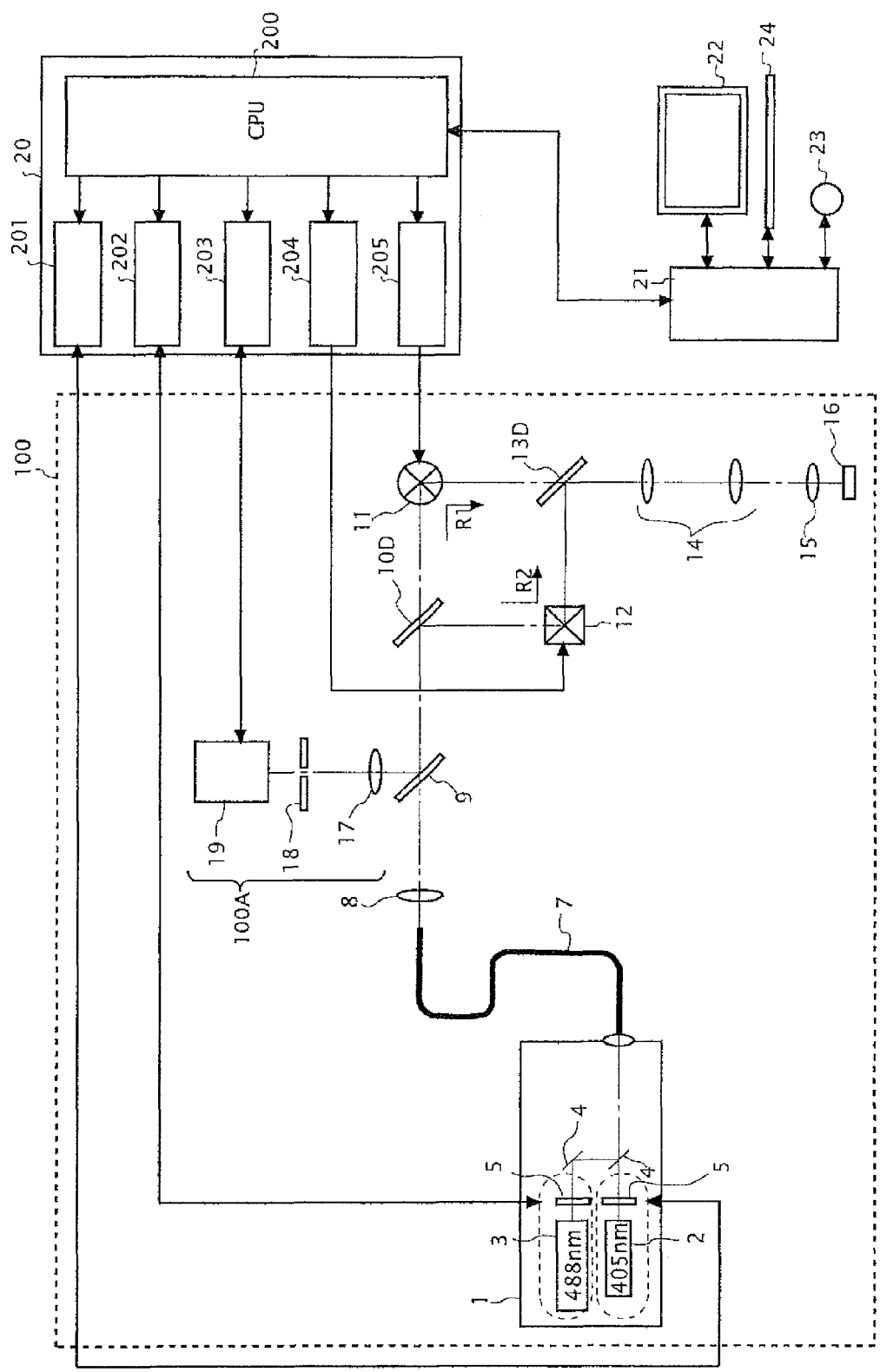
FIG. 1 is a structural view of a confocal fluorescence laser scanning microscope system.

Firstly, a structure of the present system will be described. FIG. 1 is a structural view of the present system. As shown in FIG. 1, the present system includes a main body of microscope 100, a control box 20, a computer 21 and the like.

In the main body of microscope 100, a laser unit 1, an optical fiber 7, a collimating lens 8, a dichroic mirror 9, a dichroic mirror 10D, a galvanometer scanner for light stimulus 11, a dichroic minor 13D, a galvanometer scanner for imaging 12, a relay lens 14, an objective lens 15, a sample 16, a collecting lens 17, a pinhole diaphragm for confocal detection 18, a light detector 19 and the like are disposed. Note that the sample 16 is a sample for fluorescence observation supported on a not-shown stage, and a fluorescent dye is previously added thereto.

The galvanometer scanner for light stimulus 11 is provided with a controllable galvanometer minor for main scanning and a controllable galvanometer minor for vertical scanning which are disposed in serial relationship. Such a galvanometer scanner for light stimulus 11 can freely set an irradiation target.

The galvanometer scanner for imaging 12 is provided with a resonant galvanometer mirror for main scanning and a controllable galvanometer mirror for vertical scanning which are disposed in serial relationship. Such a galvanometer scanner for imaging 12 scans at a high speed.

A laser light source for light stimulus 2 (wavelength of 405 nm) and a laser light source for imaging 3 (wavelength of 488 nm) are mounted on the laser unit 1. An excitation wavelength of the aforementioned fluorescent dye is substantially the same as an emission wavelength of the laser light source for imaging 3 (wavelength of 488 nm).

Laser light for light stimulus emitted from the laser light source for light stimulus 2 and laser light for imaging emitted from the laser light source for imaging 3 respectively pass through light modulation devices 5, and after that, they are combined by combining mirrors 4 and emitted from the laser unit 1.

The Laser lights emitted from the laser unit 1 are incident on one end of the optical fiber 7. The laser lights propagate inside the optical fiber 7, and then the lights are emitted from the other end of the optical fiber 7, and after being turned into parallel pencil of light by the collimating lens 8, they are incident on the dichroic mirror 9. The laser lights pass through the dichroic mirror 9 and are incident on the dichroic mirror 10D. Out of the laser lights incident on the dichroic mirror 10D, the laser light for light stimulus transmits through the dichroic mirror 10D, and the laser light for imaging is reflected by the dichroic mirror 10D.

The laser light for light stimulus transmitted through the dichroic mirror 10D passes through a light path R1, and after being reflected by the galvanometer scanner for light stimulus 11, it is incident on the dichroic mirror 13D. A characteristic of the dichroic minor 13D is set in the same manner as a characteristic of the dichroic mirror 10D, so that the laser light for light stimulus passed through the light path R1 transmits through the dichroic mirror 13D, passes through the relay lens 14 and the objective lens 15, and forms a spot on the sample 16. When the galvanometer scanner for light stimulus 11 is driven under this state, the spot moves over the sample 16.

Meanwhile, the laser light for imaging reflected by the dichroic mirror 10D passes through a light path R2 which is different from the light path R1, and after being reflected by the galvanometer scanner for imaging 12, it is incident on the dichroic mirror 13D. Since the characteristic of the dichroic mirror 13D is set in the same manner as the characteristic of the dichroic mirror 10D, the laser light for imaging passed through the light path R2 is reflected by the dichroic mirror 13D, passes through the relay lens 14 and the objective lens 15, and forms a spot on the sample 16. When the galvanometer scanner for imaging 12 is driven under this state, the spot moves over the sample 16.

In the spot, namely, the spot formed on the sample 16 by the laser light for imaging, a fluorescence whose wavelength is longer than that of the laser light is generated. The fluorescence advances in the opposite direction along the same light path as that of the laser light for imaging which forms the spot, and reaches the dichroic mirror 9 via the objective lens 15, the relay lens 14, the dichroic mirror 13D, the galvanometer scanner for imaging 12, and the dichroic mirror 10D. The fluorescence is reflected by the dichroic mirror 9, collected by the collecting lens 17 of an optical system for detecting 100A, and is directed to the pinhole diaphragm 18. Out of the fluorescence, the one passed through the pinhole diaphragm 18 is incident on the light detector 19 and converted into an electrical signal.

The light detector 19, together with the laser light source for light stimulus 2, the laser light source for imaging 3, the galvanometer scanner for light stimulus 11, and the galvanometer scanner for imaging 12 are controlled by the control box 20.

The control box 20 is provided with a laser controlling circuit for light stimulus 201, a laser controlling circuit for imaging 202, a detection controlling circuit 203, a scanner controlling circuit for imaging 204, a scanner controlling circuit for light stimulus 205, and a CPU 200.

The laser controlling circuit for light stimulus 201 performs power control and on-off controlling of the laser light for light stimulus emitted from the laser unit 1. The laser controlling circuit for imaging 202 performs power control and on-off controlling of the laser light for imaging emitted from the laser unit 1. The detection controlling circuit 203 performs drive control of the light detector 19, and acquires the electrical signal generated by the light detector 19. The scanner controlling circuit for imaging 204 performs drive control of each of the two galvanometer mirrors of the galvanometer scanner for imaging 12, and the scanner controlling circuit for light stimulus 205 performs drive control of each of the two galvanometer mirrors of the galvanometer scanner for light stimulus 11.

The CPU 200 previously sets a power and an emitting pattern of the laser light for light stimulus in the laser controlling circuit for light stimulus 201. Thereafter, when the CPU 200 gives a drive instruction to the laser controlling circuit for light stimulus 201, the laser controlling circuit for light stimulus 201 makes the laser light for light stimulus emit with the set power and the set emitting pattern.

Further, the CPU 200 previously sets a power and an emitting pattern of the laser light for imaging in the laser controlling circuit for imaging 202. Thereafter, when the CPU 200 gives a drive instruction to the laser controlling circuit for imaging 202, the laser controlling circuit for imaging 202 makes the laser light for imaging emit with the set power and the set emitting pattern.

Further, the CPU 200 previously sets an angular variation pattern of the two galvanometer mirrors of the galvanometer scanner for imaging 12 in the scanner controlling circuit for imaging 204. Thereafter, when the CPU 200 gives a drive instruction to the scanner controlling circuit for imaging 204, the scanner controlling circuit for imaging 204 drives the two galvanometer mirrors of the galvanometer scanner for imaging 12 with the set angular variation pattern.

Further, the CPU 200 generates drive data to be given to the two galvanometer mirrors of the galvanometer scanner for light stimulus 11, and gives the data to the scanner controlling circuit for light stimulus 205. At this time, the scanner controlling circuit for light stimulus 205 D/A converts the drive data given by the CPU 200 to transmit it to the two galvanometer mirrors of the galvanometer scanner for light stimulus 11.

Accordingly, in the present embodiment, the two galvanometer mirrors of the galvanometer scanner for light stimulus 11 are directly driven by the CPU 200 in real time.

Note that an imaging area on the sample 16 is set in accordance with a combination of the power and the emitting pattern of the laser light for imaging and the angular variation pattern of the two galvanometer mirrors of the galvanometer scanner for imaging 12. By giving, under the setting, the drive instruction to the laser controlling circuit for imaging 202, the detection controlling circuit 203, and the scanner controlling circuit for imaging 204, the CPU 200 can perform imaging on the predetermined imaging area on the sample 16 with the predetermined power. The electrical signal generated by the light detector 19 during this imaging is acquired by the CPU 200 as an image via the detection controlling circuit 203. In the present embodiment, this imaging is repeatedly conducted at high speed (sequentially imaging).

Further, when the CPU 200 drives, after previously setting the power and the emitting pattern of the laser light for light stimulus, the two galvanometer mirrors of the galvanometer scanner for light stimulus 11, and then gives the drive instruction to the laser controlling circuit for light stimulus 201, it can apply the light stimulus to any point on the sample 16 with the predetermined power and the predetermined emitting pattern. In the present embodiment, this light stimulus is performed during a period of the sequentially imaging (simultaneous stimulus).

To the computer 21, a monitor 22, a mouse 23, and a keyboard 24 are connected. Further, a software of the present system (software operated under a GUI environment) is previously installed in the computer 21. The computer 21 displays a GUI image on the monitor 22 in accordance with the software. By operating the mouse 23 and the keyboard 24 while checking the GUI image, a user can input a condition for the sequentially imaging, a condition for the light stimulus, a start operation of the light stimulus observation and the like into the computer 21.

Figure 2:
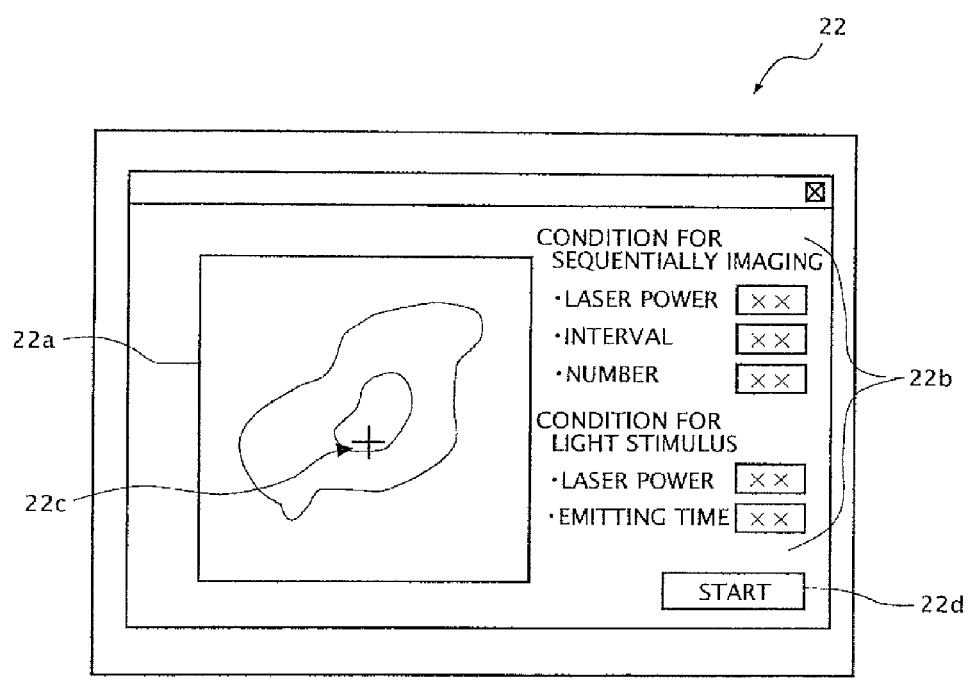
FIG. 2 is a view showing a display screen of a monitor 22 at a time of light stimulus observation.

Next, an operation of the present system at the time of light stimulus observation will be described in detail. FIG. 2 is a view showing a display screen of the monitor 22 at the time of light stimulus observation. As shown in FIG. 2, an image displaying area 22a, an information displaying area 22b, a start button 22d, a cursor 22c and the like are disposed on the display screen.

The image displaying area 22a is an area on which an image of the sample 16 is displayed. Before the start of the light stimulus observation, an image of the sample 16 obtained through pre-imaging (pre-image) is displayed.

On the information displaying area 22b, the condition for the sequentially imaging, the condition for the light stimulus and the like are displayed as character information. The condition for the sequentially imaging includes a power, a frequency (interval) of the imaging, a number of imaging and the like of the laser light for imaging, and the condition for the light stimulus includes a power, an emitting time and the like of the laser light for light stimulus. The aforementioned conditions are examples of possible irradiating conditions which may be input by a user.

When the user positions the cursor 22c over an input box of the information displaying area 22b through a displace operation of the mouse 23 and performs a clicking operation of the mouse 23, it becomes possible to input the condition into the computer 21. The computer 21 transmits, when the condition is input therein, the condition to the CPU 200. Upon receiving the condition, the CPU 200 performs various settings on the laser controlling circuit for light stimulus 201, the laser controlling circuit for imaging 202, the detection controlling circuit 203, and the scanner controlling circuit for imaging 204, in accordance with the condition.

Incidentally, in the normal light stimulus observation, the interval of the sequentially imaging is set to be sufficiently short (1/30 sec, for instance), and the emitting time of the laser light for light stimulus is set to any period of time from a sufficiently short period of time to a long period of time (0.1 msec to 10 sec, for instance).

Further, when the user positions the cursor 22c over the start button 22d through the displace operation of the mouse 23 and performs the clicking operation of the mouse 23, the start operation of the light stimulus observation is input into the computer 21.

Figure 3:
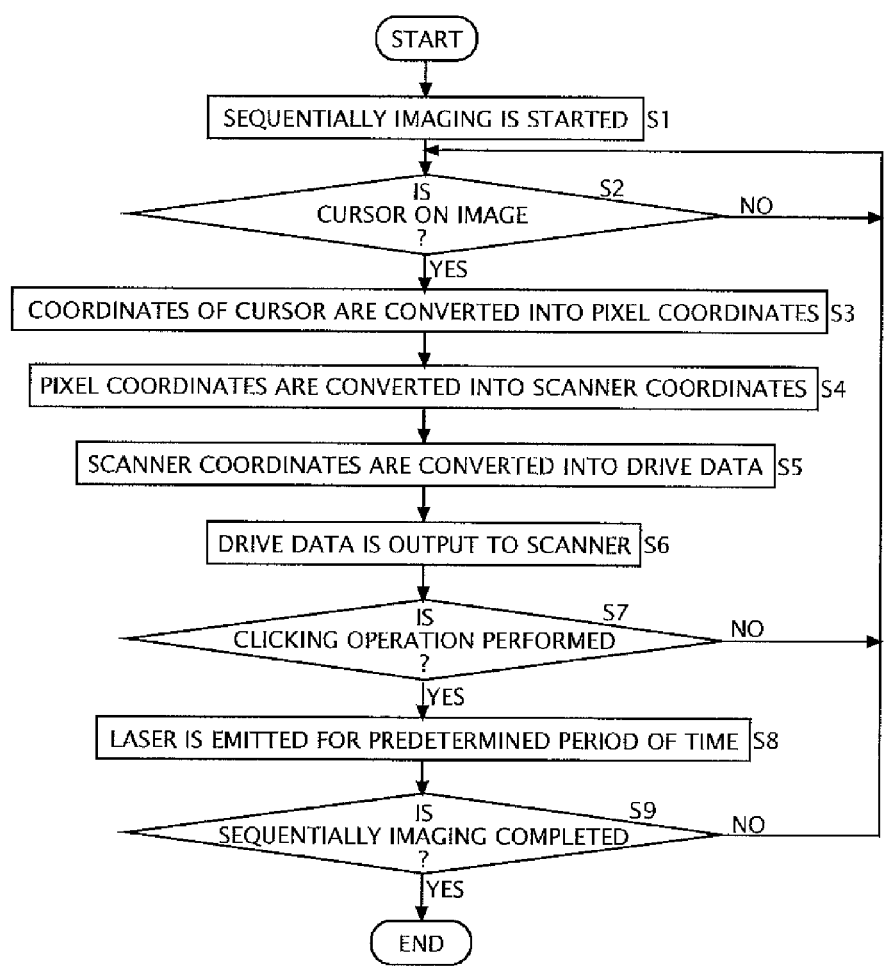
FIG. 3 is an operational flow chart of a system of a first embodiment at a time of light stimulus observation.

FIG. 3 is an operational flow chart of the present system at the time of light stimulus observation. Note that in FIG. 3, an operation of the computer 21 and an operation of the control box 20 are shown with no distinction, for the sake of simplicity. Hereinafter, respective steps will be described in a sequential order.

Step S1: The computer 21 transmits, when the start operation of the light stimulus observation is input from a user, the start operation of the sequentially imaging to the CPU 200. Upon receiving the start operation of the sequentially imaging, the CPU 200 starts to perform the sequentially imaging under the present setting, and sequentially transfers the images of the sample 16 obtained through the sequentially imaging to the computer 21. At this time, a power of the laser light for imaging irradiated to the sample 16 is a power previously input by the user, and an interval of the sequentially imaging is an interval previously input by the user.

The computer 21 sequentially displays the images transferred from the CPU 200 on the image displaying area 22a of the monitor 22. Since the interval of the sequentially imaging is sufficiently short as described above, a live image of the sample 16 is displayed on the image displaying area 22a at this time.

Step S2: The computer 21 determines whether or not the cursor 22c exists on the live image (in the image displaying area 22a), in which when the cursor exists on the live image, the process proceeds to step S3, and when it exists out of the live image, step S2 is executed again.

Step S3: The computer 21 converts coordinates of the cursor 22c (which designates a point area) on the monitor 22 (pointer coordinates) into coordinates on the live image (pixel coordinates).

Step S4: The computer 21 converts the pixel coordinates into coordinates of the galvanometer scanner for light stimulus 11 (scanner coordinates), and transmits the scanner coordinates to the CPU 200. Note that when the imaging area can be freely set by the user, a size and an offset amount of the set imaging area are taken into consideration at this conversion.

Step S5: The CPU 200 generates drive data to be given to the galvanometer scanner for light stimulus 11 by multiplying the received scanner coordinates by a coefficient, and gives the drive data to the scanner controlling circuit for light stimulus 205.

Step S6: The scanner controlling circuit for light stimulus 205 D/A converts the drive data given by the CPU 200 to generate a drive voltage, and transmits the voltage to the galvanometer scanner for light stimulus 11. Accordingly, angles of the two galvanometer mirrors of the galvanometer scanner for light stimulus 11 are controlled to values corresponding to the position of the cursor 22c on the live image.

Step S7: The computer 21 determines whether or not the clicking operation of the mouse 23 is performed, in which when the clicking operation is performed, the process proceeds to step S8, and when it is not performed, the process goes back to step S2.

Step S8: The computer 21 transmits the start operation of the light stimulus to the CPU 200. Upon receiving the start operation of the light stimulus, the CPU 200 starts to apply the light stimulus under the present setting (upon receiving the start operation of the light stimulus, the CPU 200 generates drive data to be given to the light modulation device 5, gives the drive data to the laser controlling circuit for light stimulus 201, D/A converts the drive data to generate a drive voltage, and transmits the voltage to the light modulation device 5 of the laser light source for light stimulus 2). At this time, a power of the laser light for light stimulus irradiated to the sample 16 is a power previously input by the user, and an emitting time of the laser light for light stimulus is an emitting time previously input by the user. Further, an irradiating position of the laser light for light stimulus on the sample 16 coincides with the current disposed position of the cursor 22$c$ on the live image.

Step S9: The computer 21 determines whether or not the number of imaging up to that time reaches the number of imaging previously input by the user, in which when the number reaches the previously input number, the flow is terminated, and when it does not reach the previously input number, the process goes back to step S2.

As described above, in the present system, the position of the cursor 22$c$ on the live image is reflected on the angles of the two galvanometer mirrors of the galvanometer scanner for light stimulus 11 (steps S3 to S6).

Accordingly, the user of the present system can apply the light stimulus to the same position on the sample 16 only by disposing the cursor 22$c$ on a desired position on the live image and then performing the clicking operation of the mouse 23.

Besides, the steps for reflecting the position of the cursor 22$c$ on the angles of the galvanometer mirrors (steps S3 to S6) are carried out at high speed, so that the angles of the galvanometer mirrors are set to follow-up the position of the cursor 22$c$ in real time.

Therefore, no time lag is caused from when the user disposes the cursor 22$c$ on the desired position to when the application of light stimulus can be started.

Further, the present system waits for the start operation of the light stimulus while repeatedly conducting steps S3 to S6 (step S7), so that the aforementioned time lag is not caused even when the user repeatedly applies the light stimulus to the same portion on the sample 16 or sequentially applies the light stimulus to a plurality of portions on the sample 16.

Note that as shown in FIG. 2, the condition for the light stimulus capable of being set by the user includes only two items of "power" and "emitting time" in the present system (refer to FIG. 2), but, an item of "type of emitting pattern" can be added to the condition. In such a case, it is possible to allow the user to select either of "pulse pattern" and "sequential pattern". Further, when the "pulse pattern" is selected, it is possible to allow the user to set contents of the pulse pattern (a pulse width and an interval).

Further, although an area shape of the light stimulus that is carried out by the click of the mouse 23 in the present system is a spot shape on the sample corresponding to the position of cursor on the image, but, it can be a shape previously registered by the user (a line, a polygon, or a free shape), and in such a case, the position clicked by the mouse 23 indicates a center or a barycentric position of the registered shape.

[Second Embodiment]

Hereinafter, a second embodiment will be described. The present embodiment is also an embodiment of a confocal fluorescence laser scanning microscope system. Here, only a difference from the first embodiment will be described.

The difference is in the operation of the computer 21 and the control box 20. The CPU 200 of the control box 20 directly performs an on/off of the laser light for light stimulus in real time, instead of previously setting the emitting pattern of the laser light for light stimulus in the laser controlling circuit for light stimulus 201. In accordance with that, in the present embodiment, the item of "emitting time" is excluded from the condition for the light stimulus capable of being set by the user (refer to FIG. 2).

Figure 4:
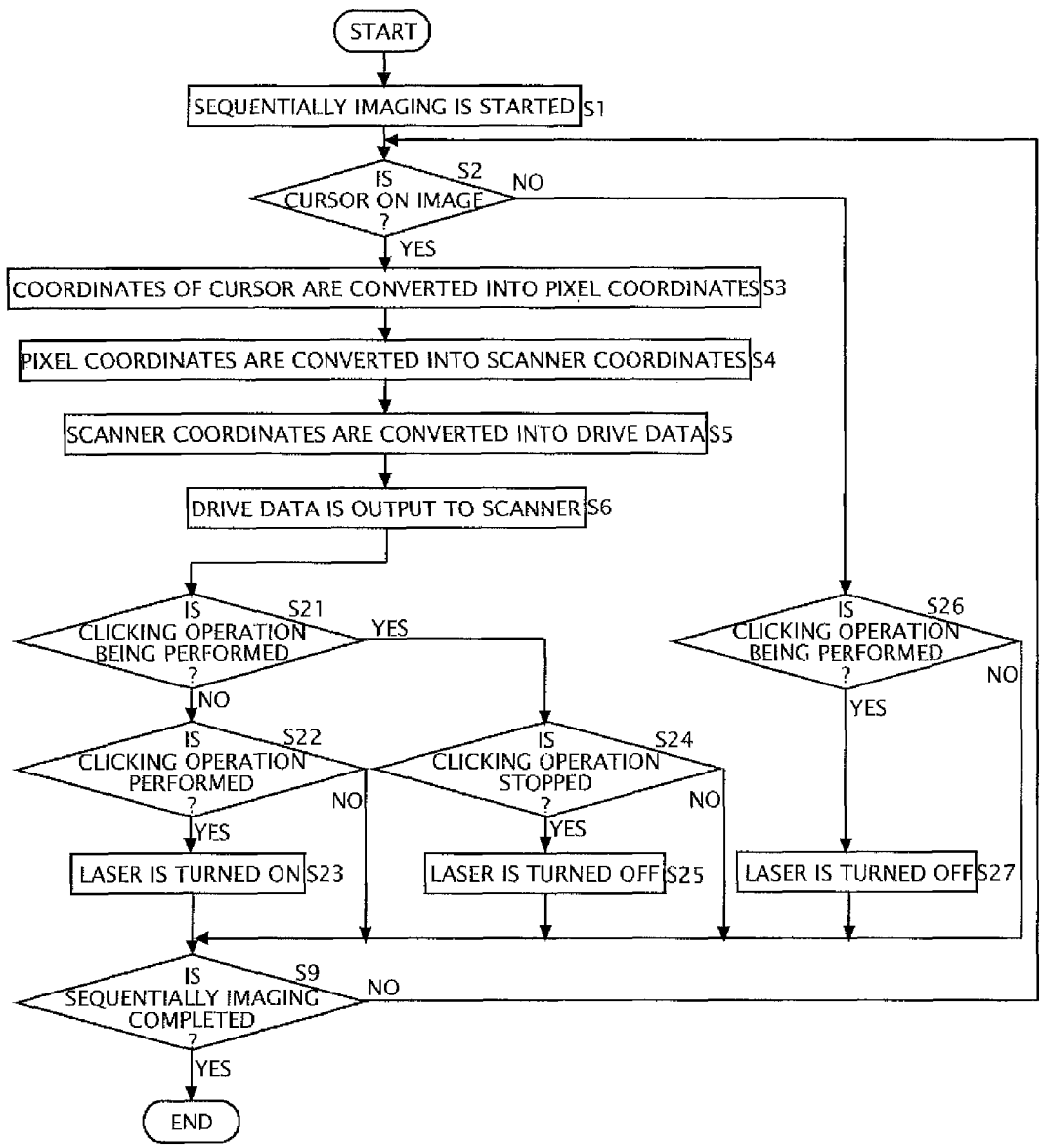
FIG. 4 is an operational flow chart of a system of a second embodiment at a time of light stimulus observation.

FIG. 4 is an operational flow chart of the present system at the time of light stimulus observation. Note that also in FIG. 4, an operation of the computer 21 and an operation of the control box 20 are shown with no distinction, for the sake of simplicity. Hereinafter, respective steps will be described in a sequential order.

Step S1: The computer 21 transmits, when the start operation of the light stimulus observation is input from a user, the start operation of the sequentially imaging to the CPU 200. Upon receiving the start operation of the sequentially imaging, the CPU 200 starts to perform the sequentially imaging under the present setting, and sequentially transfers the images of the sample 16 obtained through the sequentially imaging to the computer 21. At this time, a power of the laser light for imaging irradiated to the sample 16 is a power previously input by the user, and an interval of the sequentially imaging is an interval previously input by the user.

The computer 21 sequentially displays the images transferred from the CPU 200 on the image displaying area 22$a$ of the monitor 22. Since the interval of the sequentially imaging is sufficiently short as described above, a live image of the sample 16 is displayed on the image displaying area 22$a$ at this time.

Step S2: The computer 21 determines whether or not the cursor 22$c$ exists on the live image (in the image displaying area 22$a$), in which when the cursor exists on the live image, the process proceeds to step S3, and when it exists out of the live image, the process proceeds to step S26.

Step S3: The computer 21 converts coordinates of the cursor 22$c$ on the monitor 22 (pointer coordinates) into coordinates on the live image (pixel coordinates).

Step S4: The computer 21 converts the pixel coordinates into coordinates of the galvanometer scanner for light stimulus 11 (scanner coordinates), and transmits the scanner coordinates to the CPU 200. Note that when the imaging area can be freely set by the user, a size and an offset amount of the set imaging area are taken into consideration at this conversion.

Step S5: The CPU 200 generates drive data to be given to the galvanometer scanner for light stimulus 11 by multiplying the received scanner coordinates by a coefficient, and gives the drive data to the scanner controlling circuit for light stimulus 205.

Step S6: The scanner controlling circuit for light stimulus 205 D/A converts the drive data given by the CPU 200 to generate a drive voltage, and transmits the voltage to the galvanometer scanner for light stimulus 11. Accordingly, angles of the two galvanometer mirrors of the galvanometer scanner for light stimulus 11 are controlled to values corresponding to the position of the cursor 22$c$ on the live image.

Step S21: The computer 21 determines whether or not the clicking operation of the mouse 23 is performed, in which when the clicking operation is not performed, the process proceeds to step S22, and when it is performed, the process proceeds to step S24.

Step S22: The computer 21 determines whether or not the clicking operation of the mouse 23 is started, in which when the clicking operation is started, the process proceeds to step 23, and when it is not started, the process proceeds to step S9.

Step S23: The computer 21 transmits the start operation of the light stimulus to the CPU 200. Upon receiving the start operation of the light stimulus, the CPU 200 turns on the laser light for light stimulus under the present setting (upon receiving the start operation of the light stimulus, the CPU 200 generates drive data to be given to the light modulation device 5, gives the drive data to the laser controlling circuit for light stimulus 201, D/A converts the drive data to generate a drive voltage, and transmits the voltage to the light modulation device 5 of the laser light source for light stimulus 2). At this time, a power of the laser light for light stimulus irradiated to the sample 16 is a power previously input by the user, and an irradiating position of the laser light for light stimulus on the sample 16 coincides with the current disposed position of the cursor 22c on the live image.

Step S24: The computer 21 determines whether or not the clicking operation of the mouse 23 is stopped, in which when the clicking operation is stopped, the process proceeds to step S25, and when it is not stopped, the process proceeds to step S9.

Step S25: The computer 21 transmits an end instruction of the light stimulus to the CPU 200. Upon receiving the end instruction of the light stimulus, the CPU 200 turns off the laser light for light stimulus.

Step S26: The computer 21 determines whether or not the clicking operation of the mouse 23 is performed, in which when the clicking operation is not performed, the process proceeds to step S9, and when it is performed, the process proceeds to step S27.

Step S27: The computer 21 transmits the end instruction of the light stimulus to the CPU 200. Upon receiving the end instruction of the light stimulus, the CPU 200 turns off the laser light for light stimulus.

Step S9: The computer 21 determines whether or not the number of imaging up to that time reaches the number of imaging previously input by the user, in which when the number reaches the previously input number, the flow is terminated, and when it does not reach the previously input number, the process goes back to step S2.

As described above, steps S1 to S6 similar to those in the system of the first embodiment are executed in the present system. Accordingly, the aforementioned time lag is not caused also in the present system.

Further, in the present system, the laser light for light stimulus is turned on during a period of time in which the cursor 22c is positioned on the live image and the mouse 23 is clicked, but, during a period of time in which the cursor 22c is positioned on the live image and the mouse 23 is not clicked, the laser light for light stimulus is turned off. Therefore, in the present system, the emitting pattern of the laser light for light stimulus interlocks with a pattern of the clicking operation of the mouse 23.

Accordingly, the user of the present system can make the laser light for light stimulus emit at a desired pattern only by appropriately performing the clicking operation of the mouse 23.

For instance, when the light stimulus is tried to be applied to a certain line on the sample 16, the user is only required to trace the line on the live image with the cursor 22c while clicking the mouse 23. The line can be linear or curved.

Further, when the light stimulus is tried to be applied to a certain area on the sample 16, the user is only required to mark out the area on the live image with the cursor 22c while clicking the mouse 23.

[Third Embodiment]

Hereinafter, a third embodiment will be described. The present embodiment is an embodiment of a confocal fluorescence laser scanning microscope system. Here, only a difference from the first embodiment and the second embodiment will be described.

The difference is that the control for reflecting the angles of galvanometer mirrors on the position of the cursor 22c is performed only when a user clicks the mouse 23, instead of conducting the follow-up control of the galvanometer scanner 11 in real time in accordance with the movement of the cursor 22c.

Figure 5:
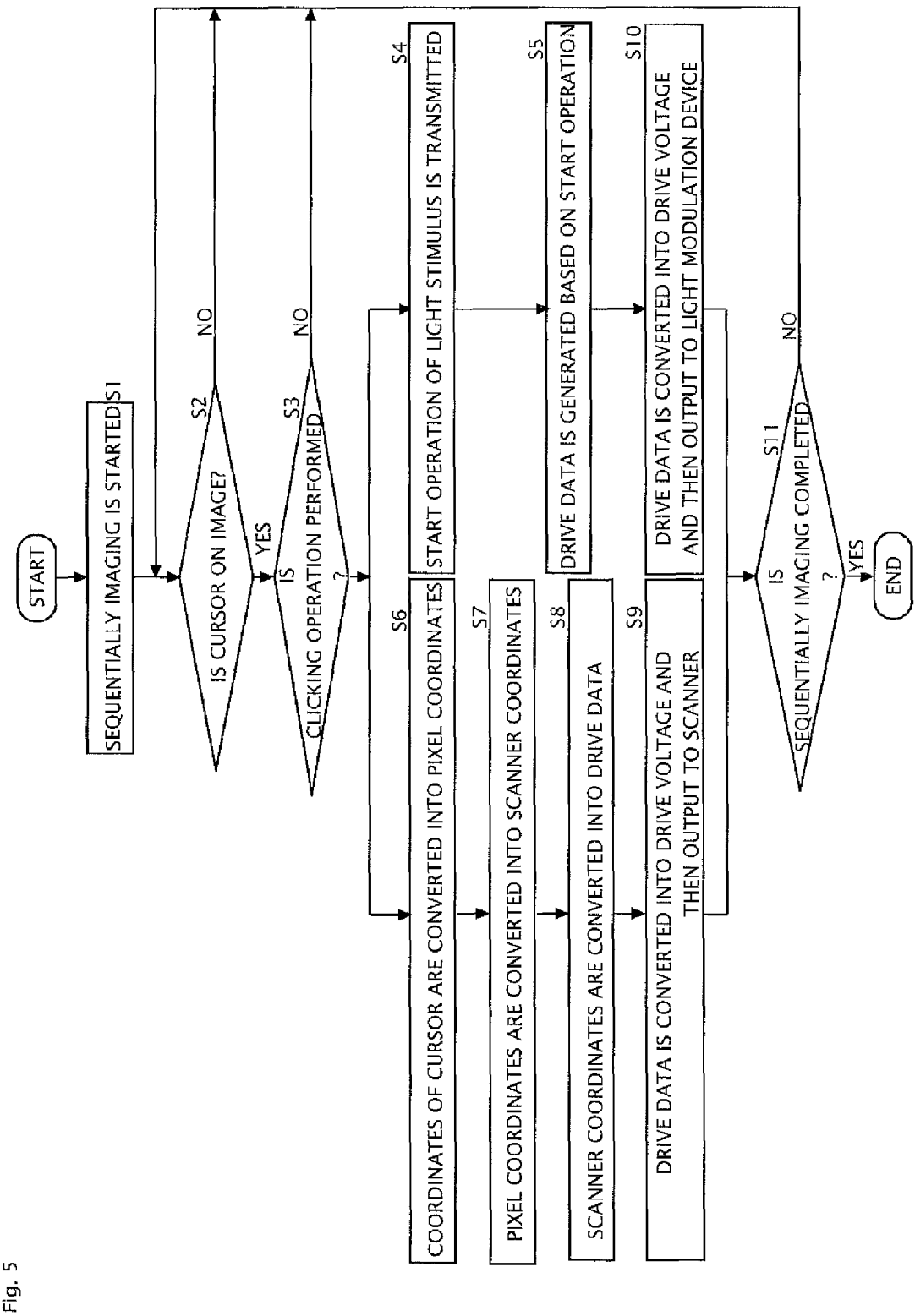
FIG. 5 is an operational flow chart of a system of a third embodiment at a time of light stimulus observation.

FIG. 5 is an operational flow chart of the present system at the time of light stimulus observation. Note that also in FIG. 5, an operation of the computer 21 and an operation of the control box 20 are shown with no distinction, for the sake of simplicity. Hereinafter, respective steps will be described in a sequential order.

Step S1: The computer 21 transmits, when the start operation of the light stimulus observation is input from a user, the start operation of the sequentially imaging to the CPU 200. Upon receiving the start operation of the sequentially imaging, the CPU 200 starts to perform the sequentially imaging under the present setting, and sequentially transfers the images of the sample 16 obtained through the sequentially imaging to the computer 21. At this time, a power of the laser light for imaging irradiated to the sample 16 is a power previously input by the user, and an interval of the sequentially imaging is an interval previously input by the user.

The computer 21 sequentially displays the images transferred from the CPU 200 on the image displaying area 22a of the monitor 22. Since the interval of the sequentially imaging is sufficiently short as described above, a live image of the sample 16 is displayed on the image displaying area 22a at this time.

Step S2: The computer 21 determines whether or not the cursor 22c exists on the live image (in the image displaying area 22a), in which when the cursor exists on the live image, the process proceeds to step S3, and when it exists out of the live image, step S2 is carried out again.

Step S3: The computer 21 determines whether or not the clicking operation of the mouse 23 is performed, in which when the clicking operation is performed, the process proceeds to step S4, and when it is not performed, the process goes back to step S2.

Step S4: When the clicking operation of the mouse 23 is performed, the computer 21 transmits the start operation of the light stimulus to the CPU 200, while concurrently performing later-described step S6.

Step S5: Upon receiving the start operation of the light stimulus, the CPU 200 generates drive data to be given to the light modulation device 5 based on the start operation of the light stimulus, and gives the drive data to the laser controlling circuit for light stimulus 201.

Step S6: When the clicking operation of the mouse 23 is performed, the computer 21 converts coordinates of the cursor 22c (which designates a point area) on the monitor 22 (pointer coordinates) into coordinates on the live image (pixel coordinates), while concurrently performing step S4.

Step S7: The computer 21 converts the pixel coordinates into coordinates of the galvanometer scanner for light stimulus 11 (scanner coordinates), and transmits the scanner coordinates to the CPU 200. Note that when the imaging area can be freely set by the user, a size and an offset amount of the set imaging area are taken into consideration at the time of this conversion.

Step S8: The CPU 200 generates drive data to be given to the galvanometer scanner for light stimulus 11 by multiplying the received scanner coordinates by a coefficient, and gives the drive data to the scanner controlling circuit for light stimulus 205.

Step S9: The scanner controlling circuit for light stimulus 205 D/A converts the drive data given by the CPU 200 to generate a drive voltage, and transmits the voltage to the galvanometer scanner for light stimulus 11. Accordingly, angles of the two galvanometer mirrors of the galvanometer scanner for light stimulus 11 are controlled to values corresponding to the position of the cursor 22c on the live image. When the setting of the galvanometer mirrors is completed, a setting completion signal is transmitted to the laser controlling circuit for light stimulus 201.

Step S10: Upon receiving the setting completion signal of the galvanometer mirrors, the laser controlling circuit for light stimulus 201 D/A converts the drive data given by the CPU 200 to generate a drive voltage, and transmits the voltage to the light modulation device 5 of the laser light source for light stimulus 2. Accordingly, the application of light stimulus is started under the present setting. At this time, a power of the laser light for light stimulus irradiated to the sample 16 is a power previously input by the user, and an emitting time of the laser light for light stimulus is an emitting time previously input by the user. Further, an irradiating position of the laser light for light stimulus on the sample 16 coincides with the current disposed position of the cursor 22c on the live image.

Step S11: The computer 21 determines whether or not the number of imaging up to that time reaches the number of imaging previously input by the user, in which when the number reaches the previously input number, the flow is terminated, and when it does not reach the previously input number, the process goes back to step S2.

[Other Embodiments]

Note that in the system of the aforementioned embodiments, in order to notify the user of a position on the sample 16 to which the light stimulus is applied, a mark such as a dot mark can be displayed at a position of the cursor 22c at the time when the clicking operation of the mouse 23 is performed. Incidentally, when the light stimulus is applied to a line, a line-shaped mark is displayed.

Further, in the main body of microscope 100 of the aforementioned embodiments, a part of the light path of the laser light for light stimulus and that of the light path of the laser light for imaging are shared, but, the light paths can be independently provided. For example, all the light paths from the laser light sources 2 and 3 to the dichroic mirror 13D can be independently provided.

Further, although the light stimulus is applied during the period of sequentially imaging in the system of the aforementioned embodiments, it is possible to design such that the sequentially imaging is started right after the application of light stimulus. In such a case, the user examines a position on the sample 16 to which the light stimulus is applied, on a pre (still) image instead of on the live image.

Further, as a type of cursor, a crosshair cursor is used on the aforementioned display screen (refer to FIG. 2), but, another type of cursor such as an arrow cursor can also be used.

Further, in the main body of microscope 100 of the above-described embodiments, the galvanometer scanner 12 is used for scanning the sample 16 with the laser light for imaging, but, another type of scanner such as a Nipkow disk can also be used instead of the galvanometer scanner.

Further, the main body of microscope 100 of the aforementioned embodiments is a fluorescence microscope that performs imaging of the sample 16 based on the fluorescence emitted from the sample 16, but, it may be a reflection-type or transmission-type microscope that performs imaging of the sample 16 based on reflected illumination light or transmitted illumination light emitted from the sample 16.

Further, the main body of microscope 100 of the aforementioned embodiments is a confocal microscope that performs confocal detection on the light emitted from the sample 16 via the pinhole diaphragm 18, but, it may be a non-confocal microscope that detects the light emitted from the sample 16 with no aid of the pinhole diaphragm 18. In such a case, it is possible to perform the imaging of the sample 16 in a collective manner instead of performing the imaging of the sample 16 through the light scanning. Further, when the imaging is performed in a collective manner, it is possible to collectively illuminate an observation area on the sample 16 and to use an imaging element instead of the light detector 19.

Further, in the system of the aforementioned embodiments, a mouse is used as a pointing device, but, another pointing device such as a joystick, a touch pad, a touch panel, a stylus pen, a trackball, a data glove, a light pen, and a joy pad can also be used. Further, a specific key on the keyboard can be used to serve a part or all of the functions of the pointing device.

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to the exact construction and operation illustrated and described, and accordingly all suitable modifications and equivalents may be resorted to, falling within the scope thereof.

What is claimed is:

1. A light stimulus apparatus, comprising:
a light controlling unit that controls an irradiating timing of light for stimulus to a specimen; and
a light path controlling unit that controls an irradiating position of the light for stimulus on the specimen;
wherein:
the light path controlling unit allows the irradiating position on the specimen to coincide with a position where a pointing device points on an image of the specimen that is displayed on a displaying unit, and
the light controlling unit irradiates the light for stimulus simultaneously when a confirm operation of the position being pointed to on the image of the specimen is performed.

2. The light stimulus apparatus according to claim 1, wherein:
the confirm operation of the pointed position is a clicking operation of the pointing device.

3. The light stimulus apparatus according to claim 1, wherein:
the image is a live image of the specimen.

4. The light stimulus apparatus according to claim 2, further comprising:
a condition designating unit allowing a user to designate in advance an irradiating condition of the light for stimulus to the specimen, wherein:
the irradiating condition includes an emitting pattern of the light for stimulus.

5. An observing apparatus, comprising:
an optical imaging apparatus obtaining an image of the specimen; and
the light stimulus apparatus according to claim 1 irradiating the light for stimulus onto the specimen.

6. The observing apparatus according to claim 5, wherein:
the imaging apparatus is a scanning imaging apparatus provided with a light path controlling unit for imaging; and
the light path controlling unit of the light stimulus apparatus is operable independently from the light path controlling unit for imaging.

\* \* \* \* \*